United States Patent [19]
Musikant et al.

[11] Patent Number: 5,803,732
[45] Date of Patent: Sep. 8, 1998

[54] SLOTTED TAP AND LENTULO DRILL FOR DENTAL POST SYSTEM

[75] Inventors: Barry Musikant, Tenafly, N.J.; Allan S. Deutsch, New York; Brett I. Cohen, Nanuet, both of N.Y.

[73] Assignee: Essential Dental Systems, Inc., South Hackensack, N.J.

[21] Appl. No.: 789,389

[22] Filed: Jan. 29, 1997

Related U.S. Application Data

[63] Continuation-in-part of Ser. No. 645,263, May 13, 1996, Pat. No. 5,632,620, which is a continuation-in-part of Ser. No. 381,428, Jan. 31, 1995, abandoned.

[51] Int. Cl.⁶ .................................................. A61C 5/02
[52] U.S. Cl. ............................................. 433/102; 433/81
[58] Field of Search ............................. 433/81, 102, 224, 433/165, 166

[56] References Cited

U.S. PATENT DOCUMENTS

| | | |
|---|---|---|
| 498,554 | 5/1893 | Johanson . |
| 4,536,156 | 8/1985 | Cattin ...................................... 433/10 C |
| 5,632,620 | 5/1997 | Musikant et al. ..................... 433/165 X |

FOREIGN PATENT DOCUMENTS

| | | | |
|---|---|---|---|
| 581004 | 9/1932 | Germany ................................ 433/102 |
| 837146 | 4/1952 | Germany ................................ 433/102 |

*Primary Examiner*—Nicholas D. Lucchesi
*Attorney, Agent, or Firm*—Gottlieb, Rackman & Reisman, P.C.

[57] ABSTRACT

A method and system for inserting a dental post into a tooth root canal is provided. The method comprises the steps of cutting out a post hole in the tooth and inserting a threaded tap into the post hole for creating at least one groove along the hole. Significantly, the tap includes at least one slot defined by a pair of flexible legs and running at least a portion of the length thereof for reducing stress along the post hole during threaded insertion. Also provided is a lentulo drill comprising a spiraled wire with a reverse spiral configuration at the apical end thereof for confining cement placement in the post hole prior to insertion of the dental post.

7 Claims, 3 Drawing Sheets

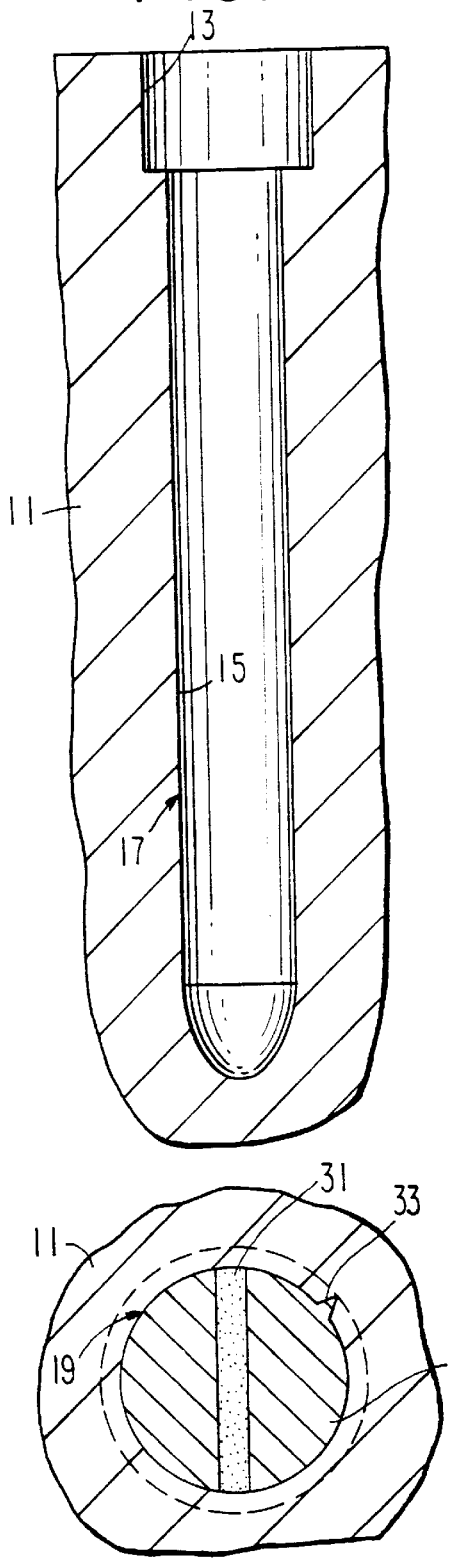
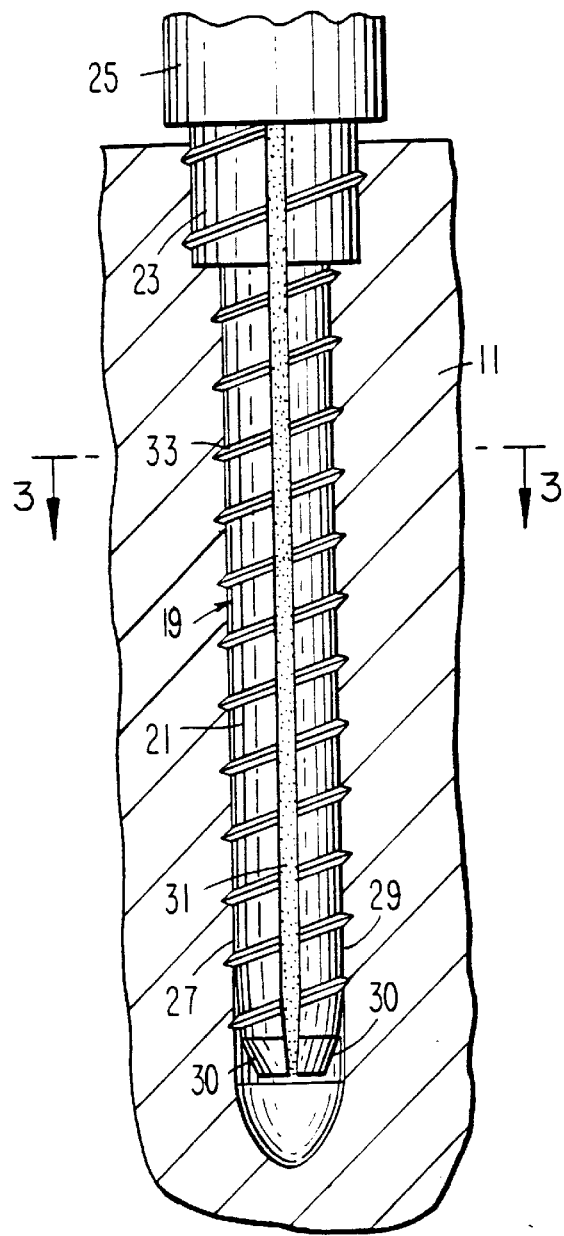
FIG.1
FIG.2
FIG.3

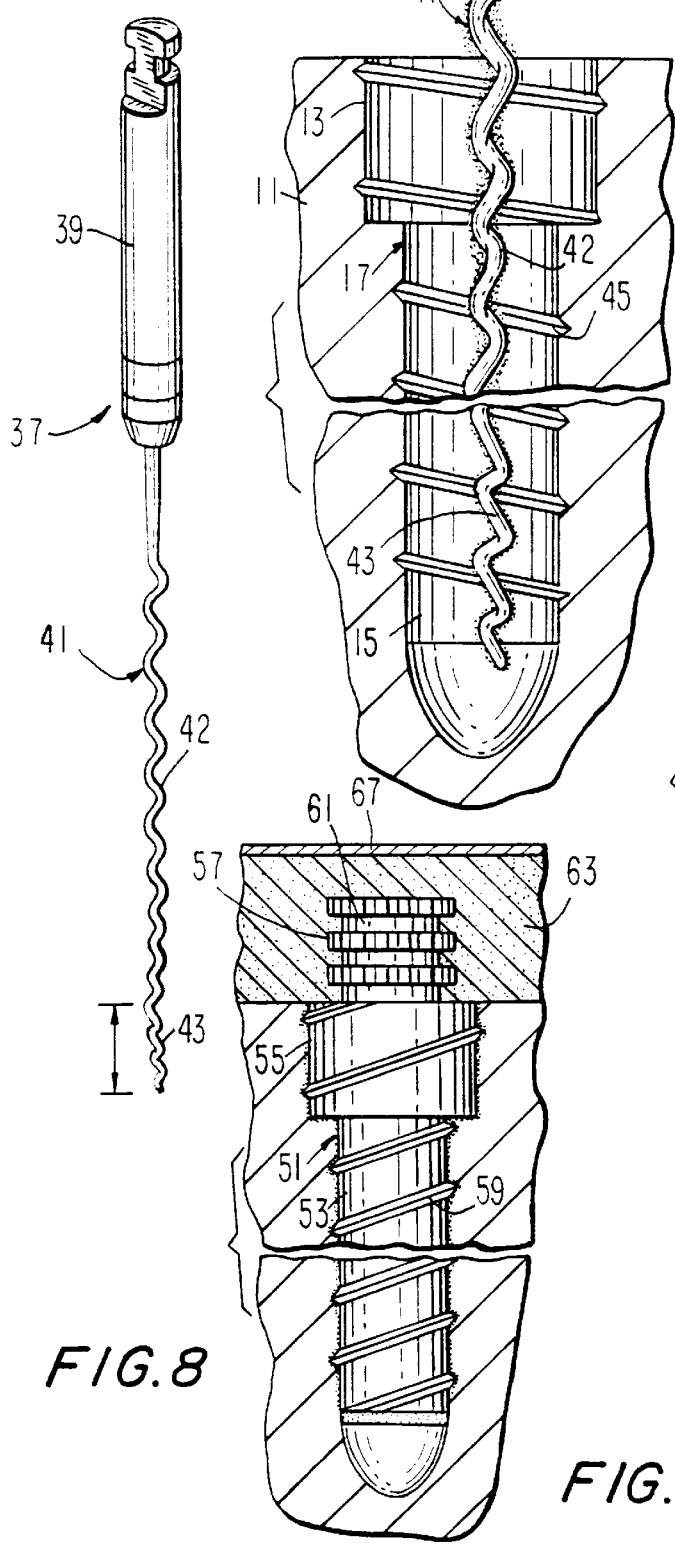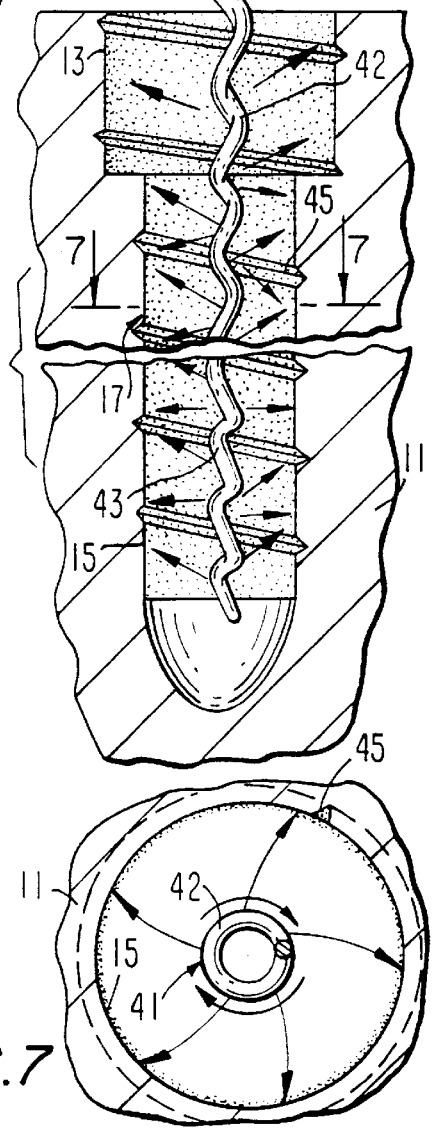
FIG. 4
FIG. 5
FIG. 6
FIG. 7
FIG. 8

SLOTTED TAP AND LENTULO DRILL FOR DENTAL POST SYSTEM

This application is a CIP of 08/645,263, filed May 13, 1996, now U.S. Pat. No. 5,632,620, which is a CIP of 08/381,428, filed Jan. 31, 1995, now abandoned.

BACKGROUND OF THE INVENTION

This invention relates to a novel method for placing a dental post into a tooth root canal, and more particularly, to a dental post system that utilizes a slotted tap and a reverse lentulo drill.

In conventional root canal techniques, it is generally the practice to first form a post-hole in a selected tooth, after which a dental prefabricated post is placed therein. Then, the dentist or dental practitioner builds up the core using a core build-up material, after which a crown is applied thereover.

One example of a prefabricated post is the product FLEXI-POST, manufactured by Essential Dental Systems, Inc. of South Hackensack, N.J. and described in U.S. Pat. Nos. 4,490,116 and RE 31,948. This dental post has a threaded outside for generating grooves into the post hole of a tooth as the post is threadingly inserted therein. The product also has relatively spaced legs that define a longitudinally extending slot. The legs move radially to absorb threading torque and other forces. Therefore, the legs prevent the application of such forces and stresses to the walls of the tooth root so as to permit the dental post to be threaded without fracture of the tooth. In other words, threading the post into the root canal causes the slot of the post to at least partially collapse, thereby reducing stress while the post is being threaded. However, the use of a slotted post such as FLEXI-POST does have certain disadvantages. Since FLEXI-POST is not a solid post, there is the risk of increased metal fatigue.

In many systems used in dentistry today, a substantially solid tap is used to trial thread a root canal. The purpose of the tap is to create the grooves along the post hole in the root canal. Once this is done, a solid post is seated in the post hole in which the grooves were formed by the threads of the previously used tap.

Although at first examination, it would appear that use of a solid tap would produce less stress during insertion than if one simply took a solid threaded post and trial seated it into the root canal. However, use of such a solid tap for creating grooves in the post hole does apply a significant amount of force and stress to the walls of the tooth root, and there is still a risk of fracture to the tooth when using a tap. This is because there is substantially no flexibility between the tooth and the thread formed along the post-hole.

Another problem with most dental post systems is the difficulty of applying cement along the post hole prior to insertion of the dental post. In some systems, a lentulo drill is used, which essentially comprises a spiral wire which sprays cement radially along the post hole. In other words, if the end or apex of the post hole is open, the cement can often be sprayed by the lentulo drill wire beyond the confines of the post hole. This is because of the centrifying action of the spiral—no stop is found on a conventional lentulo drill.

Accordingly, it would be desirable to provide a dental post system including a tap and lentulo drill which overcomes these disadvantages.

SUMMARY OF THE INVENTION

Generally speaking it accordance with the invention, a method and system for inserting a dental post into a tooth root canal is provided. The method comprises the steps of cutting out a post hole in the tooth and inserting a threaded tap into the post hole for creating at least one groove along the hole. Significantly, the tap includes at least one slot defined by a pair of flexible legs and running at least a portion of the length thereof for reducing stress along the post hole during threaded insertion.

Thereafter, the tap is unthreaded from the post hole in order to reveal at least one groove that was formed by the slotted tap which runs along the post hole. Cement is placed either along the post hole or on the post itself and the post is finally threaded into the post hole.

In practice, the slotted tap comprises a depending shaft and at least one flange located adjacent the shaft with a diameter that is larger than the diameter of the shaft. The tap is adapted to be received in the post hole with the flange seated along an annular tier formed in the hole. In this situation, and since size, shape and configuration of the post must be substantially similar to that of the tap, the post also includes a depending shaft and at least one flange to be selectively seated along the annular tier formed in the post hole.

The advantage of using the dental system of the invention is to prevent the application of forces and stress to the walls of the post hole when forming the necessary groove or grooves therealong for the dental post. Also, since a solid post is threaded, the dental restoration is stronger and more resistant to metal fatigue.

As part of the invention, a specially designed lentulo drill is used to radially apply cement to the wall of the post hole prior to insertion of the dental post. The lentulo drill comprises a spiraled wire having a reverse spiral configuration along the most apical end thereof. This reverse spiral acts as a stop on the apical whipping of the cement during operation of the drill, thereby confining the placement of the cement to the length of the post hole along which the dental post is to be inserted.

Accordingly, it would be desirable to provide an improved dental post system for a tooth root canal.

Another object of the invention is to provide a dental tap having a slot running at least a portion of the length thereof for preventing the application of forces and stress to the walls of the post hole.

A further object of the invention is to provide a system for a dental root canal which utilizes a slotted tap and a substantially solid post.

Yet another object of the invention is to provide a dental post system for a dental root canal in which cement is applied to the post hole utilizing a lentulo drill with a reverse spiral on the most apical end.

Still other objects and advantages of the invention will in part be obvious, and will in part be apparent from the following description.

The invention accordingly comprises the several steps and the relation of one or more such steps with respect to each of the others, the system embodying the features of construction, combination of elements, and arrangement of parts which are adapted to effect such steps, and the product or products which possess the characteristics, properties and relation of components, all as exemplified in the detailed disclosure hereinafter set forth, and the scope of the invention will be indicated in the claims.

DESCRIPTION OF THE DRAWINGS

For a fuller understanding of the invention, reference is made to the following description, taken in connection with the accompanying drawings, in which:

FIG. 1 is plan view in partial cross-section showing formation of a post hole in a tooth having an elongated shaft and a shortened tier;

FIG. 2 is plan view in partial cross-section illustrating the threaded slotted tap of the invention after it has been threaded into the tooth post hole;

FIG. 3 is a cross-sectional view taken along line 3—3 of FIG. 2;

FIG. 4 is a plan view illustrating the lentulo drill of the invention with the reverse spiral wire at its apical tip;

FIG. 5 is a broken plan view in partial cross-section illustrating insertion of the spiral wire of the lentulo tip into the post hole of the tooth;

FIG. 6 is a broken plan view in partial cross-section similar to FIG. 5, but illustrating operation of the lentulo drill as the wire thereof radially sprays cement along the wall of the post hole;

FIG. 7 is a cross-sectional view taken along line 7—7 of FIG. 6; and

FIG. 8 is a broken plan view in partial cross-section showing a substantially solid post after it has been threadingly inserted into the post hole of the tooth and with core material and a crown applied thereover.

DETAILED DESCRIPTION OF THE PREFERRED EMBODIMENTS

Figure 9:
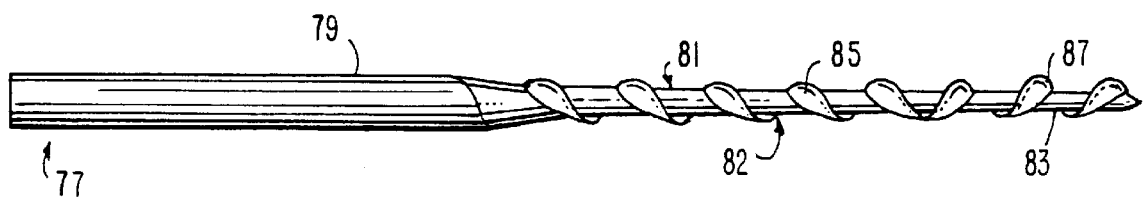
FIG. 9 is a side elevational view of an alternative embodiment of the lentulo drill of the invention.

Referring first to FIG. 1, a post hole generally indicated at 17 is shown formed in a tooth 11. Post hole 17 is typically prepared by means of a cutting drill, a primary reamer and a countersink drill bit, as is well known in the art. The cutting drill is first used to prepare the post hole. The primary reamer is used next and comprises a rotating shaft which is contained in a conventional dental drill. The primary reamer is drilled into the post hole in order to widen the post hole to the desired diameter. The countersink drill bit comprises a shaft and a head having a plurality of annularly spaced teeth and the countersink drill bit is used in order to cut one or more preparations in the post hole. As shown in FIG. 1, post hole 17 includes a bore 15 and a tier 13. For a further description of the use of a cutting drill, a primary reamer and countersink drill, reference is made to U.S. Pat. No. 5,348,476 to Cohen et al.

Turning now to FIGS. 2 and 3, a slotted tap 19 in accordance with the invention is shown. Slotted tap 19 comprises a shaft 21 formed unitarily with a body or flange member 23 that is connected to head 25. Shaft 21, body 23 and head 25 are all integrally connected together and formed as a unitary structure with a continuously running thread 33 formed along shaft 21 and body 23. Thread 33 is used to create a continuously running groove along the wall of post hole 15, as described below. Tap 19 is preferably made from stainless steel, titanium or titanium alloy.

Shaft 21 is divided and separated into a desired plurality of substantially flexible legs exemplified in the drawing by two legs 27 and 29. Legs 27 and 29 are relatively spaced by a slot 31 that extends fully along the length of the shaft and body 23 where it terminates at head 25. Slot 31 is sized such as to permit legs 27 and 29 to absorb radial forces that are applied to the legs when shaft 19 is threaded into post hole 17, as shown in FIG. 2.

In particular, tap 19 is selected in size to match the size of post hole 17 that was prepared by the primary reamer and countersink drill, as described above. Slotted tap 19 is threadingly inserted into post hole 17 by rotating head 25 in a conventional manner, preferably by hand, until tips 30 of legs 29 reach the apical end of post hole 15. Dental debris is collected in slot 31, as shown in FIG. 2, as tap 19 is threaded in post hole 17, which is later removed when tap 19 is unthreaded.

By using tap 19 of the invention, a continuously running groove (see FIG. 5) is formed along the wall of post hole 15. Moreover, since legs 27 and 29 are flexible and spaced apart by slot 31, the legs absorb the threading torque and other forces produced during the threading operation in order to prevent the application of such forces and stresses to the wall of post hole 17. Consequently, the risk of fracture to tooth 11 is substantially reduced.

If the tap 19 does not fully seat in post hole 17 such that body 23 is not in the hole, it would be necessary to apically cut the tap along shaft 21 to seat the tap appropriately. This results in a threaded pattern that is appropriate for both tier 13 and bore 15.

Once threading of post hole 17 is completed, tap 19 is then unthreaded therefrom by rotating head 25 thereof in the opposite direction. As can be seen in FIG. 5, post hole 17, along both bore 15 and tier 13, now incorporates a running groove therealong that will be used for threadingly receiving a substantially solid dental post, as described below.

Turning now to FIG. 4, a lentulo drill, generally indicated at 37, and made in accordance with the invention, is now described. Drill 37 is used for applying a dental cement along post hole 17 and comprises a shaft 39 which can be selectively retained in a powered dental handpiece, and an extending spiral wire 41. Wire 41 comprises a main wire portion 42, and apical wire portion 43 (identified in FIG. 4).

As best shown in FIG. 5, main wire portion 42 includes a series of forward helical spirals. On the other hand, apical wire portion 43 includes a spiral wire configuration that is different from the rest of the wire 41, that is, it incorporates or comprises a reverse spiral wire configuration. In other words, main wire portion 42 will have a series of spirals which are in either a clockwise or counterclockwise rotational direction, while wire portion 43 will have a series of spirals with the opposite rotational direction. Such a configuration is used to prevent cement placement along post hole 17 beyond where the dental post is to be placed. Preferably, the reversed spiral wire configuration is no greater than 50% of the length of wire 41 that is inserted in post hole 17, as shown in FIG. 5.

In FIGS. 5–7, operation of lentulo drill 37 for applying a dental cement to post hole 17 is now described. Spiral wire 41 of drill 37 is inserted into post hole 17 (which now includes running groove 45 formed by tap 19) until the tip of wire 41 is located just below where post hole 17 begins to narrow (see FIG. 5). Then, lentulo drill 37 is operated in order to rapidly rotate spiral wire 41, as shown in FIG. 7. Spiral wire 41, as alluded to above, has been previously dipped in or otherwise applied with an appropriate dental cement that is suitable for dental post application. Consequently, when wire 41 rotates, the applied cement is radially sprayed from wire 41 to the wall of post hole 17. With respect to wire portion 42, cement is sprayed radially in both a somewhat upward and downward direction (see arrows in top portion of FIG. 6). However, because apical wire portion 43 has a reverse spiral configuration, cement is only radially sprayed therefrom in either a slightly up or sideways direction (see arrows in bottom portion of FIG. 6)—no cement is sprayed below where post hole 17 along bore 15 begins to narrow. Thus, cement is placed only along the portion of the post hole where the dental post is to be inserted.

Once cement application is complete, and referring to FIG. 8, a substantially solid dental post generally indicated at 51 is selected which matches the size of the post hole that has been prepared. The dental post is made from stainless steel, titanium, titanium alloy or gold. Dental post 51 comprises a body 55 sized to sit along tier 13 of post hole 17, an extending shaft 53 and a head 57. Shaft 53 and body 55 are formed with a continuous thread 59 which runs therealong and which is sized to engage running groove 45 formed along the wall of post hole 17. In use, post 51 is threadingly inserted into post hole 17 until head 57 sits flush along the surface of tooth 11, body 55 rests along tier 13 and the end of shaft 53 is disposed along post hole 17 where post hole 17 begins to narrow—see FIG. 8.

In concluding the root canal procedure, a core material 63 is built up over head 57 of post 51, which may include a series of grooves 61 (vertical and horizontal) for facilitating engagement with the core material. Then, a crown 67 is placed over core material 63 in a conventional fashion.

Although in the preferred system, the lentulo drill is used to apply cement along the wall of the post hole prior to insertion of the dental post, cement may instead be applied to the wall of the post hole by means of a dental instrument or explorer, as is well known. Alternatively, the dental post to be inserted can be first painted or otherwise applied with a cement prior to insertion in the post hole.

In an alternative embodiment, drill 37, illustrated in FIGS. 4–7, may be replaced by lentulo drill 77, as best depicted in FIG. 9. Drill 77, like drill 37, is used for applying a dental cement along a post hole and/or a root canal and comprises a shaft 79 (which can be selectively retained in a powered dental handpiece) and an extending wire bar 81. Bar 81 is substantially tubular in design and comprises a main bar portion 82 and an apical bar portion 83. As best shown in FIG. 9, main bar portion 82 includes a series of forward helical spirals 85 separated by depressions running about the surface thereof, while apical bar portion 83 includes a series of reverse helical spirals 87 separated by depressions running about the surface thereof. As with drill 37, the configuration of drill 77 includes a series of spirals at the apical end having an opposite rotational direction, which prevents cement placement along a post hole and/or root canal beyond where the dental post or dental gutta percha is placed.

Manufacture of drill 77 is as follows:

The depressions (valleys) between spirals 85 and 87 formed along bar 81 are formed by a machinery tool as is well known in the art.

Although the lentulo drill of the invention preferably has a reverse spiral configuration along its most apical end, the reverse spiral configuration could extend beyond the apical end and even along substantially all of the entire wire.

It will thus be seen that the objects set forth above, among those made apparent from the preceding description, are efficiently attained and, since certain changes may be made in carrying out the above process, in the described products, and in the construction set forth above, without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention described herein, and all statements of the scope of the invention which, as a matter of language, might be said to fall therebetween.

We claim:

1. A lentulo drill comprising a shaft and a longitudinally extending wire bar of substantially uniform dimension in a longitudinal direction with forward and apical ends and having a first portion thereof running from the forward end to a location between said forward and apical ends, said first portion including a series of helical spirals running about the surface thereof in either a clockwise or counterclockwise rotational direction, and a second portion thereof running from said location between said forward and apical ends to the apical end, said second portion including a series of reverse helical spirals running along the surface thereof in a rotational direction opposite that of said first portion, such that cement radially sprayed from said second portion when operating said drill does not spray in an apical direction.

2. The drill of claim 1, wherein said second portion has a length which is no greater than 50% of the length of said bar.

3. The lentulo drill of claim 1, wherein said wire bar is substantially cylindrical in configuration.

4. A lentulo drill comprising a shaft a longitudinally an extending member of substantially uniform dimension in a longitudinal direction with forward and apical ends, said extending member having a first portion running from the forward end to a location between said forward and apical ends, said first portion including a spiral design in either a clockwise or counterclockwise rotational direction, and a second portion thereof running from said location between said forward and apical ends to the apical end, said second portion with a reverse spiral design having a rotational direction opposite that of said first portion, such that cement radially sprayed from said second portion when operating said drill does not spray in an apical direction.

5. The drill of claim 4, wherein said extending member comprises a spiral wire, said spiral design of said first portion being defined by said first portion having a spiral configuration in one of a clockwise or counterclockwise rotational direction, and wherein said spiral design of said second portion is defined by said second portion having a reversed spiral configuration of an opposite rotational direction to that of said first portion.

6. The drill of claim 4, wherein said extending member comprises an extending wire bar, wherein said spiral design of said first portion is defined by a series of forward helical spirals running about the surface of said first portion, and said spiral design of said second portion is defined by a series of reverse helical spirals running about the surface of said second portion.

7. The drill of claim 6, wherein said extending wire bar has a substantially cylindrical configuration.

* * * * *